US010196615B2

(12) United States Patent
Vicalvi, Jr. et al.

(10) Patent No.: US 10,196,615 B2
(45) Date of Patent: Feb. 5, 2019

(54) VIRUS PURIFICATION AND FORMULATION PROCESS

(71) Applicant: GE Healthcare Bio-Sciences Corp., Marlborough, MA (US)

(72) Inventors: John J. Vicalvi, Jr., Marlborough, MA (US); Edward G. Hayman, Hanover, NH (US); Joseph Makowiecki, Oxford, MA (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 0 days.

(21) Appl. No.: 15/163,288

(22) Filed: May 24, 2016

(65) Prior Publication Data

US 2016/0264943 A1    Sep. 15, 2016

Related U.S. Application Data

(63) Continuation of application No. 14/423,394, filed as application No. PCT/US2013/055302 on Aug. 16, 2013.

(60) Provisional application No. 61/692,956, filed on Aug. 24, 2012.

(51) Int. Cl.
*C12N 7/00* (2006.01)
*A61K 39/12* (2006.01)

(52) U.S. Cl.
CPC ...... *C12N 7/00* (2013.01); *C12N 2770/24151* (2013.01); *C12N 2770/24163* (2013.01)

(58) Field of Classification Search
None
See application file for complete search history.

(56) References Cited

U.S. PATENT DOCUMENTS

| 7,320,754 B2 * | 1/2008 | Carlsson | B01D 15/363 |
| | | | 210/198.2 |
| 2005/0118698 A1 * | 6/2005 | Vorlop | C12N 7/00 |
| | | | 435/235.1 |
| 2011/0287519 A1 * | 11/2011 | Lee | A61K 39/12 |
| | | | 435/235.1 |

FOREIGN PATENT DOCUMENTS

EP    1724338 A1 * 11/2006

* cited by examiner

*Primary Examiner* — Stacy B Chen
(74) *Attorney, Agent, or Firm* — Grogan, Tuccillo & Vanderleeden, LLP (57) ABSTRACT

Disclosed herein is provided a virus purification and formulation process for purifying a flavivirus represented by one of a a Yellow Fever Virus, Japanese Encephalitis virus, Dengue virus, and West Nile virus. The highly purified flavivirus virus product is characterized as having a low level of sucrose without significant virus loss such as that which is typically encountered by prior art virus purification processes. The disclosed process captures and purifies the virus, separating it from the host cell proteins and DNA, and leaving the host cell proteins and DNA behind. The process also can be used to inactivate and/or concentrate the virus sufficiently for use in formulations.

2 Claims, 8 Drawing Sheets

VIRUS PURIFICATION AND FORMULATION PROCESS

CROSS-REFERENCE TO RELATED APPLICATIONS

This application is a continuation of U.S. application Ser. No. 14/423,394, filed on Feb. 23, 2015, which is a filing under 35 U.S.C. 371 of international application number PCT/US2013/055302, filed Aug. 16, 2013, which claims priority to U.S. Application Ser. No. 61/692,956, filed Aug. 24, 2012, the entire disclosures of each of which are hereby incorporated by reference.

FIELD OF THE INVENTION

The present invention relates generally to a method of purifying biologics, such as a virus or modified virus, and a method of formulating the biologic, for example, a virus and adjuvant.

BACKGROUND OF THE INVENTION

In order to purify a virus it is necessary to remove host cell proteins and DNA from the virus sample. Unfortunately, current methods of removing host cell proteins and DNA are accompanied by loss of a significant amount of virus. Typically, for a flavivirus, recovery of the virus from filtration processes are generally about ten to twenty percent and typically less than 10 percent. Following purification, another problem is aggregation or clumping together of the purified virus particles.

Prior art methods of purification and concentration of a virus, e.g., often use ultracentrifugation wherein sucrose is required in order to run the gradient for the separation. Such ultracentrifugation generally results in the undesirable presence of sucrose in the final virus sample. In order to obtain a virus sample that is free of sucrose, tangential flow filtration (TFF) is frequently used to separate the virus from proteins and other compounds. However, use of TFF for such a purification tends to result in significant loss of virus.

Prior art methods of purification and concentration of a virus, e.g., often use ultracentrifugation wherein sucrose is required in order to run the gradient for the separation. Such ultracentrifugation generally results in the undesirable presence of sucrose in the final virus sample. In order to obtain a virus sample that is free of sucrose, tangential flow filtration (TFF) is frequently used to separate the virus from proteins and other compounds. However, use of TFF for such a purification tends to result in significant loss of virus. As well, currently used methods of virus purification thus have been accompanied by ongoing problems including low yield or loss of virus, host cell protein levels higher than desirable, high sucrose levels, and aggregation of the purified virus particles. Such methods have also been difficult to use in single use or disposable technologies.

BRIEF SUMMARY OF THE DISCLOSURE

In accordance with the present invention there is provided a virus purification process for producing highly purified virus product having no residual sucrose without significant virus loss such as that which is typically encountered by prior art virus purification processes. The disclosed process captures and purifies the virus, separating it from the host cell proteins and DNA, and leaving the host cell proteins and DNA behind. The process also can be used to inactivate and/or concentrate the virus sufficiently for use in formulations.

Also disclosed herein is a one-step process for producing a formulation wherein the concentrated virus particles are not aggregated or clumped together. The disclosed process utilizes adjuvants and buffer exchanges to process the virus, and results in a final, buffered virus formulation. An embodiment of the process can also be used for formulation of other biologics.

BRIEF DESCRIPTION OF THE DRAWINGS

Embodiments of the invention are further described hereinafter with reference to the accompanying drawings, in which.

DETAILED DESCRIPTION OF THE PREFERRED EMBODIMENTS

The inventors of the present subject matter have now discovered a process for preparing a highly purified biological composition, such as, for example, a virus. The process is particularly useful for purifying a flavivirus, e.g., a Yellow Fever Virus, Japanese Encephalitis virus, Dengue virus, and West Nile virus. The examples provided herein are for purifying a Yellow Fever virus, but with no more than routine experimentation, could be used to purify other types of viruses.

The disclosed process significantly reduces the loss of viral particles as compared to prior art methods for obtaining a highly purified sample of a biologic. Use of an embodiment of the disclosed method also significantly lowers the amount of sucrose in the final purified product as compared to prior art methods of purification.

We now describe the development of a chromatographic process resulting in vaccine material with DNA and host cell contaminant levels at or below the level of detection while retaining high levels of virus recovery. Disclosed herein is a Yellow Fever (YF) vaccine downstream purification process designed to inactivate live YF virus, fragment Vero DNA, and remove any process contaminants, such as residual Vero host cell proteins and DNA, residual BENZONASE® and beta-Propiolactone (BPL).

YF virus may be grown on Vero cells, harvested, inactivated, and purified. Typically, prior art methods for downstream purification of a virus provide a YF virus recovery of only about 20 percent (%); and the final virus product for dosing includes a relatively high amount of Host Cell Protein (HCP). A typical YF vaccine dose for a phase 1 clinical trial may be about 0.5 milliliters (ml) of YF virus in a suspension. The remaining HCP in a dose purified by prior art methods may typically be about forty-five thousand nanograms (45,000 ng/dose) wherein the dose is about 8.3 log 10 Viral Equivalents (VE). VE is the Elisa unit for YF.

In contrast, the disclosed method provides, for the modified YF virus purification tests run to date, a downstream virus recovery of from about 30 percent to about 100 percent; and for a dose of about 0.5 milliliters (ml) of YF virus, a HCP level that is below the limit of detection of the commercially used vero cell HCP assay.

To purify the final virus product by reducing host cell proteins while maximizing virus recovery, we designed and executed a number of experiments.

Modified Yellow fever virus was prepared from the attenuated YF 17D virus available commercially as the vaccine, YF-VAX® (Sanofi Pasteur, Swiftwater Pa.). The attenuated YF 17D virus was adapted by serial passage to replicate more efficiently in Vero cells derived from the WHO Vero 10-87 Cell Bank and passaged in serum free medium. 10 serial passages were used to modify the nucleotide sequence of the viral genome virus to develop a seed virus with enhanced growth in Vero cells for preparation of an inactivated Yellow Fever virus candidate. See PCT/US2010/043010, "High Yield Yellow Fever Virus Strain With Increased Propagation In Cells", filed 23 Jul. 2010 and published 3 Feb. 2011 as WO 2011/014416, and PCT/US2011/022347, filed 25 Jan. 2011. The entire teachings of the referenced PCT applications are incorporated herein by reference.

The master and working virus seeds were manufactured from the conditioned cell culture medium harvested from stationary cultures of Vero cells prepared from the Manufacturers' Working Cell bank (MWCB). For vaccine production, the working virus seed was used to infect Vero cells prepared from the MWCB grown on CYTODEX™ 1 microcarriers in either a 50 liter, single use bioreactor (working volume 25 to 40 L) or a 10 L glass bioreactor (working volume 8 L) (Xcellerex, Inc., Marlborough, Mass.). The virus released into the cell culture medium was harvested from about 5 to about 7 days after infection. From about 2 days to about 3 days before harvest of the virus, the culture was re-fed with fresh medium. This re-feeding step has been shown to increase virus yield. See PCT/US2010/043013, "Drain Down and Re-Feed of Microcarrier Bioreactor," filed 23 Jul. 2010 and published 27 Jan. 2011 as WO 2011/011660, the entire teachings of which are incorporated herein by reference.

Figure 6:
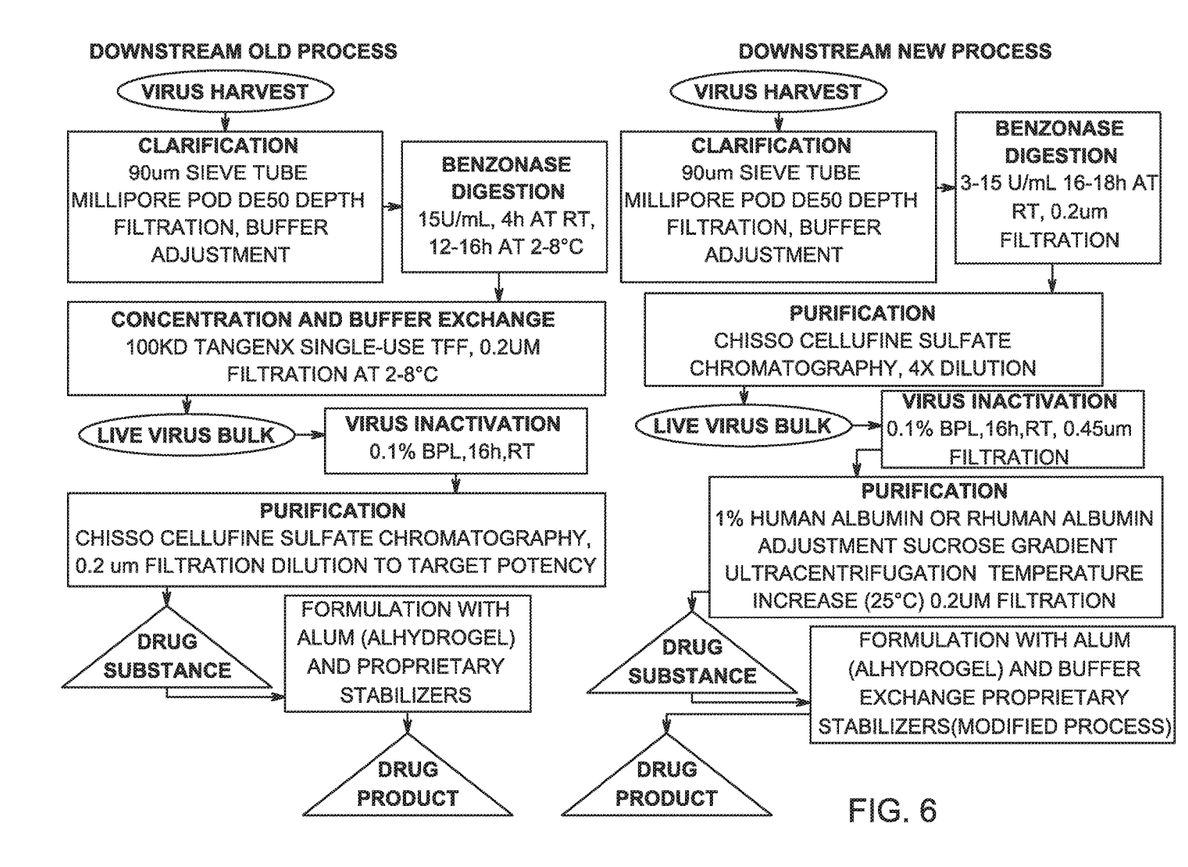
FIG. 6 is a flow diagram for an embodiment of the old downstream purification process and a flow diagram for an embodiment of the new downstream purification process.
Figure 7:
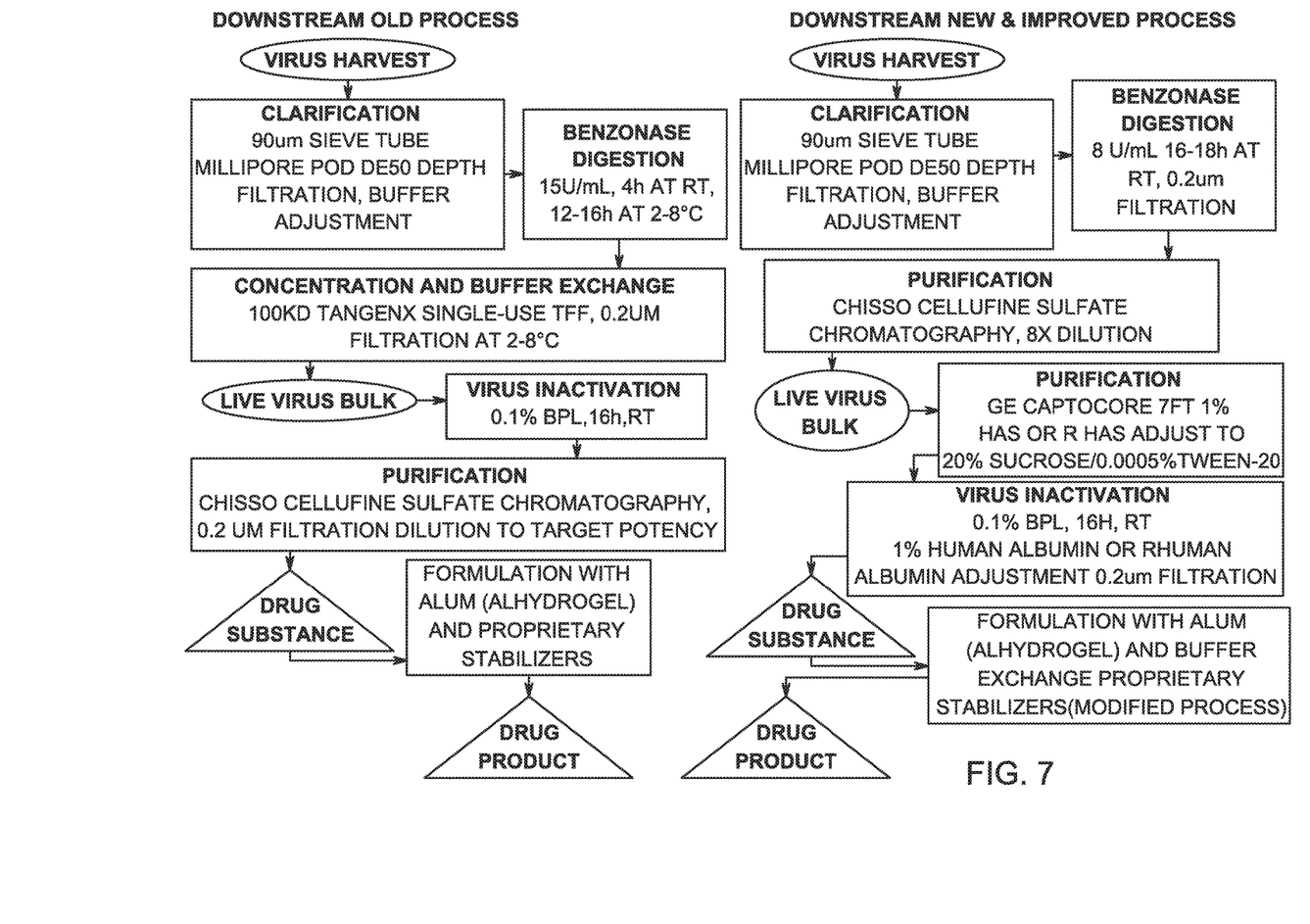
FIG. 7 is a flow diagram for the embodiment of the old downstream purification process shown in FIG. 6 and a flow diagram for an embodiment of the new and improved downstream purification process.

Some of our initial experiments in developing a purification process for the virus are schematically represented in the flow chart on the left side of each of FIG. 6 and FIG. 7, "Downstream Old Process." One set of steps was: Harvest Clarification and BENZONASE® Addition; Ultra Filtration and DiaFiltration (UF/DF); BPL Inactivation; CELLUFINE® Sulfate (Chisso Corporation, Osaka JAPAN) Column Purification; Eluate Dilution and Creation of Sub-Lots; Formulation with Alum, and Bulk Vaccine Drug Product Formulation.

Additional process development studies were initiated, with the goals of reducing residual Vero HCP; increasing overall virus recovery; removing residual sucrose in the virus sample; and minimizing aggregation of the purified virus particles. The result of the development work was an improved downstream purification process, the overall schematic of which is represented in in the flow chart on the right side of each of FIG. 6 and FIG. 7, "Downstream New Process."

In one embodiment of the invention, the New Downstream Process outlined in the right side of FIG. 6 can have the following steps, each represented by a rectangle in the Figure: Following Virus Harvest, (1) Clarification using a depth filter, and buffer adjustment. (2) BENZONASE® digestion and 0.2 Micron Filtration, producing a live virus bulk. (3) Purification using CELLUFINE® Sulfate Chromatography and Dilution for inactivation step. (4) Virus Inactivation and 0.45 Micron Filtration. (5) Sucrose Gradient UltraCentrifugation. (6) Identify Fractions; Pool Fractions; Warm to from about 25° C. to about 30° C.; 0.2 Micron Filtration, forming Bulk Drug Substance, a purified, inactivated virus. (7) Alum Binding and Formulation.

In another embodiment of the invention, the New and Improved Downstream Process outlined in the right side of FIG. 7 can have the steps as in the New Downstream Process shown in FIG. 6, with the following changes. Just prior to the virus inactivation step, there is a Purification Step using GE CAPTO™ Core 7FT with one percent (Human Serum Albumin) HSA or rHSA and adjustment to 20 percent sucrose/0.0005 percent TWEEN™-20. Then following the virus inactivation, there is an adjustment with one percent human albumin or rhuman albumin and 0.2 micron filtration to yield the bulk drug substance which can then be formulated with Alum, buffer exchange, and stabilizers.

It should be noted that the virus data determined by the 2E10 monoclonal antibody is elevated when bound to alum. While not being bound by theory, we postulated that the virus particle is arranged on the surface of the alum hydrogel so that the epitope may be presented in a more open form. Another hypothesis is that the particles are arranged in a more symmetrical manner, thus precluding the formation of aggregates which could mask epitope exposure.

These experiments indicate that the recovery of intact virus may be in some way dependent upon the presence of a small amount of "chaperone" protein. We have discovered, unexpectedly, that increasing the post sucrose gradient purified pool temperature prior to filtration results in significantly greater recovery of virus prior to alum binding, thereby resulting in an increase in virus recovery. This effect of temperature may be dependent upon the presence of the "chaperone" protein at a sufficient concentration.

Virus Harvest and BENZONASE® Treatment

The conditioned cell culture medium containing virus was removed from the bioreactor and clarified by depth filtration. A Millipore DE50 depth filter was used to clarify the Virus Harvest. The depth filter was flushed twice, once with USP purified $H_2O$ followed by buffer with the target formulation 20 mM Tris, 145 mM NaCl, pH 8. The harvest material was passed through the depth filter at a flow rate of approximately 500 mL/min and a pressure not to exceed 25 psi.

Filtered material was collected into a bioprocess single-use bag. The depth filter was chased with the same buffer and the chase volume was combined with the original filtrate. Following depth filtration, the material was adjusted to a target formulation of 50 mM Tris, pH 8 and 2 mM $MgCl2$ in preparation for the subsequent BENZONASE® treatment step. The adjusted clarified harvest was mixed for approximately 10 min at room temperature.

The adjusted clarified virus intermediate was treated with BENZONASE® in order to fragment Vero cell DNA. BENZONASE® was added to the adjusted clarified virus to a final target concentration of 3 units/mL, and the suspension was mixed for 16 to 18 hours at room temperature. After BENZONASE® treatment the product pool was 0.5 µm filtered.

CELLUFINE® Sulfate

The virus was further purified and concentrated by CELLUFINE® sulfate chromatography. CELLUFINE® sulfate (Chisso, Tokyo, Japan) is a virus affinity resin designed to concentrate, purify and depyrogenate virus. This process step significantly reduces Vero cell proteins, endotoxin and Vero cell DNA. The 2E10 ELISA that detects a YF viral envelope epitope is used to measure the virus concentration on a sample of the clarified and BENZONASE®-treated live virus to ensure the column is appropriately sized to process a virus mass challenge of no more than 5-6E+09 VE per/ml of CELLUFINE® sulfate resin.

Prior to loading the live virus material, the column was charged with 0.1 M NaoH/0.5 M NaCl buffer at an approximate linear flow rate of 200 cm/hr. The column was then equilibrated with equilibration buffer, 10 mM Tris, 145 mM NaCl, pH 7.5 at an approximate linear flow rate of 200 cm/hr. Post equilibration, the appropriate volume of the virus was loaded onto the column at an approximate linear flow rate of 200 cm/hr.

After loading, the column was washed with 10 mM Tris, 145 mM NaCl, pH 7.5 buffer at an approximate linear flow rate of 200 cm/hr. The bound virus was eluted from the column using 10 mM Tris, 1.5 M NaCl, pH 7.5 buffer at a reduced linear flow rate of approximately 100 cm/hr. Decreasing the elution flow rate increases buffer residence time and, therefore, decreases elution volume.

The elution pool was immediately diluted 2× (1 part eluate to 1 part dilution buffer) with 62.5 mM HEPES, pH 8 (target formulation) buffer to reduce precipitation of virus. Post elution, the resin was cleaned with 0.1N NaOH/0.5 M NaCl at an approximate linear flow rate of 200 cm/hr. The column was stored in 0.1N NaOH/0.5 M NaCl at room temperature.

GE CAPTO™ Core 700

The 2× diluted CELLUFINE® Sulfate elution pool was then loaded onto a CAPTO™ Core 700 column. Prior to loading, the column was regenerated with 0.1N NaOH/0.5M NaCl at a linear flow rate of 300 cm/hr. One column volume of a re-equilibration buffer of 500 mM Tris/145 mM NaCl, pH 7.5 was applied prior to the equilibration buffer consisting of 20 mM MES/100 mM NaCl, pH 7 at a linear flow rate of 300 cm/hr.

After loading, the column was washed with 20 mM MES/100 mM NaCl, pH 7 at a linear flow rate of 300 cm/hr. The flow through and wash was collected as the product. This fraction was then diluted 2× with 50 mM HEPES/20% Sucrose/0.001% TWEEN™-20, pH 8. The resin was cleaned with 1N NaOH/1M NaCl at a linear flow rate of 300 cm/hr. The column was stored in 0.1N NaOH/0.5M NaCl at room temperature.

β-PL Inactivation

A 10% solution of BPL was made by diluting BPL with water for injection (WFI). The 10% BPL was stored in single use aliquots at <−60° C. The concentration of BPL in this 10% solution was confirmed by gas chromatography (GC) analysis.

Human serum albumin (HSA) was added to the sample to adjust the concentration to 1 mg/mL HSA. A sufficient amount of 10% BPL was thawed and added while mixing to the live virus pool to bring the BPL concentration to approximately 0.1% (v/v) BPL.

The inactivation mixture was mixed for approximately 3 hours at room temperature on a low heat-generating stir plate. This material was then incubated at 30° C. for 60 minutes, and filtered using a 0.2 µm PES filter.

Alum Binding and Formulation

The 0.2 µm filtered purified inactivated virus was bound to "alum" [Aluminum aluminum Hydroxide hydroxide (Alum ALHYDROGEL®)] and buffer exchanged into the final formulation buffer. All process steps were aseptically performed.

One part of 2% Alum alum was added to 9 parts of 0.2 µm filtered sucrose gradient-purified inactivated virus to achieve a final alum target concentration of 0.2%. We refer to the resulting product as the original alum-bound virus pool. The pool was mixed for a target of 1-4 hours at room temperature.

The alum-bound virus was aseptically buffer exchanged into 10 mM Tris/1.2 mM MgCl2/10 mM L-glutamic acid/0.11 mM D-mannitol/2 mM Trimethylamine-N-oxide dihydrate, pH 7.5. The alum-bound virus was settled by centrifugation or membrane filtration. After settling, the supernatant was decanted. The alum-bound virus pellet was re-suspended with formulation buffer to a volume equal to the original alum-bound virus pool volume and mixed for a target of 10 minutes at room temperature. This process was repeated 3-4× until the alum-bound virus pool was exchanged into the final formulation buffer.

The alum-bound and buffer exchanged virus pool was stored at 2-8° C. This is referred to herein as the "Bulk Drug Product." The potency of the Bulk Drug Product was measured using ELISA that detects alum-bound YF.

Process recovery chromatograms for Experiments Y1626A, Y1632A, and Y1637A are shown in FIG. 1 through FIG. 4, respectively.

Figure 1:
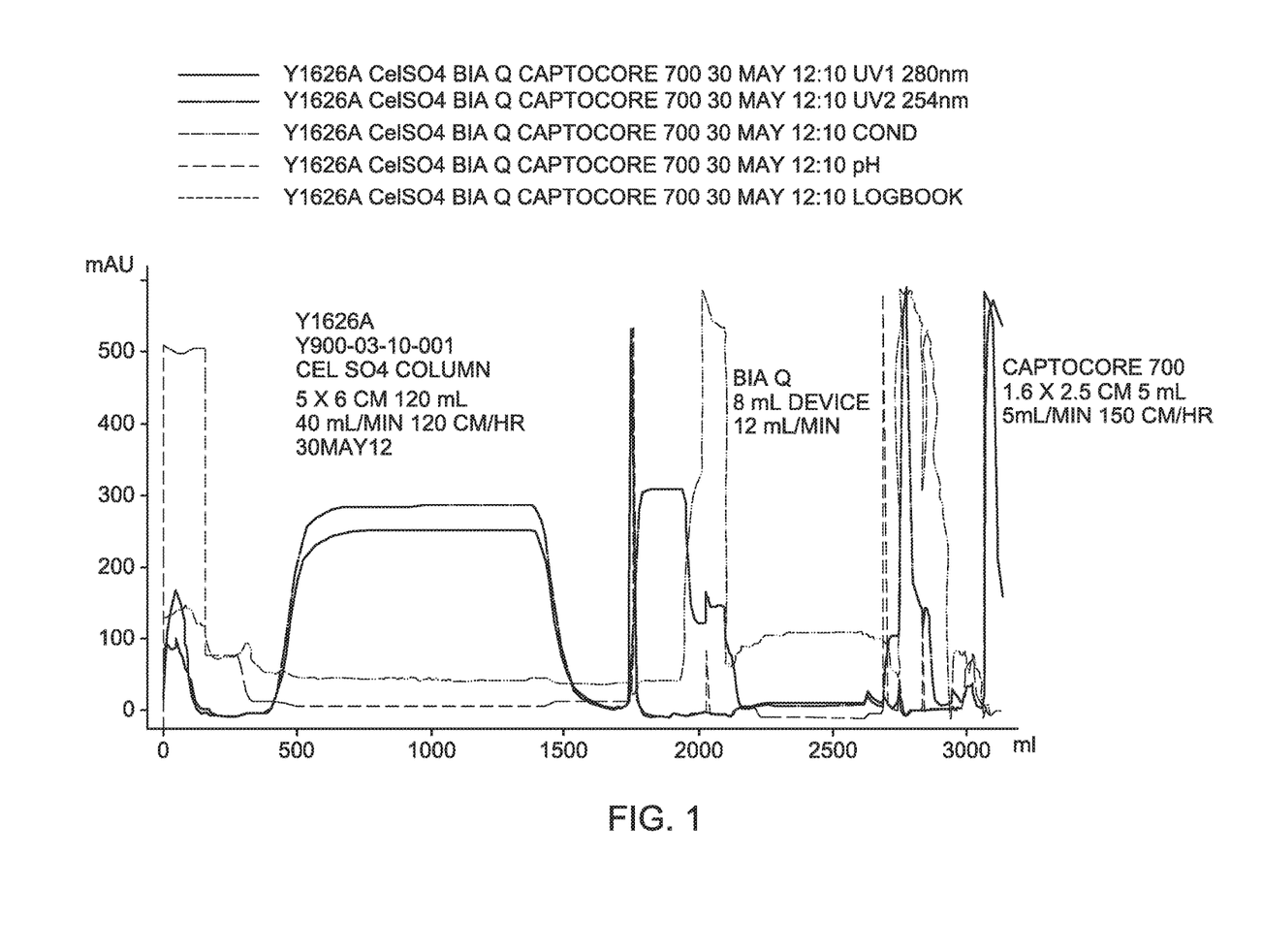
FIG. 1 is a process chromatogram for Experiment Y1626A, an embodiment of the new downstream process disclosed herein that is used to purify and formulate a harvest of modified YF virus.
Figure 2:
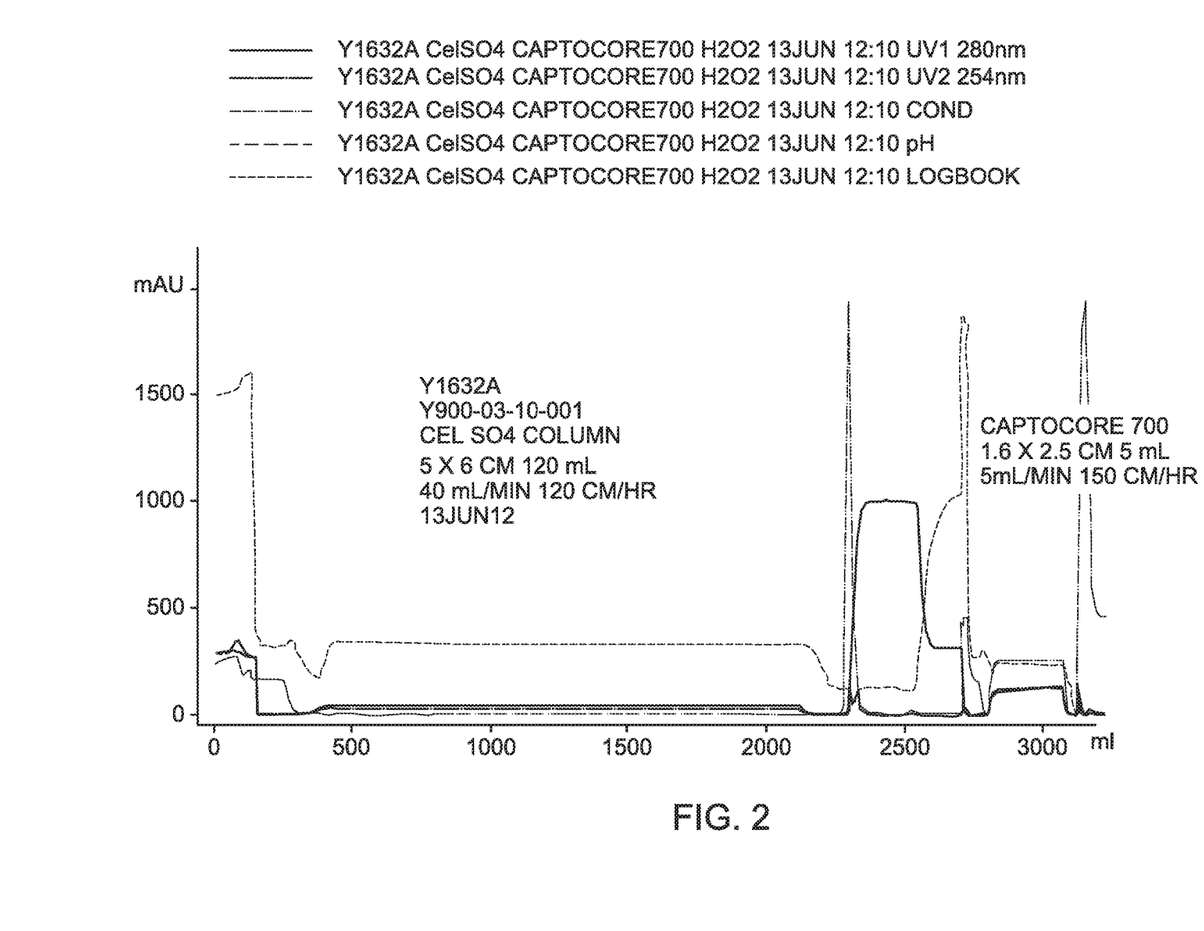
FIG. 2 is a process chromatogram for Experiment Y1632A, an embodiment of the new downstream process disclosed herein that is used to purify and formulate a harvest of modified YF virus, comparing elutions using CELLUFINE® sulphate and CAPTO™ Core 700.
Figure 3:
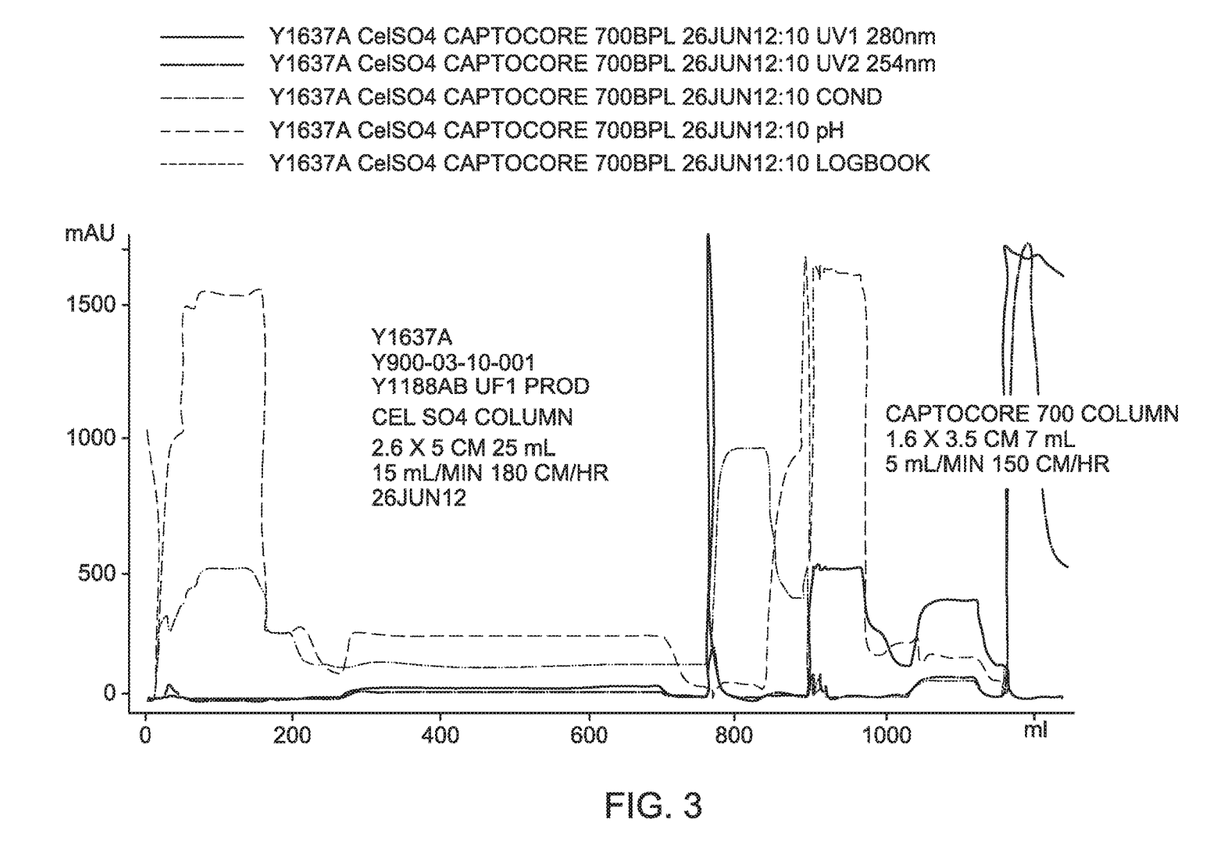
FIG. 3 is a process chromatogram for Experiment Y1637A.
Figure 4:
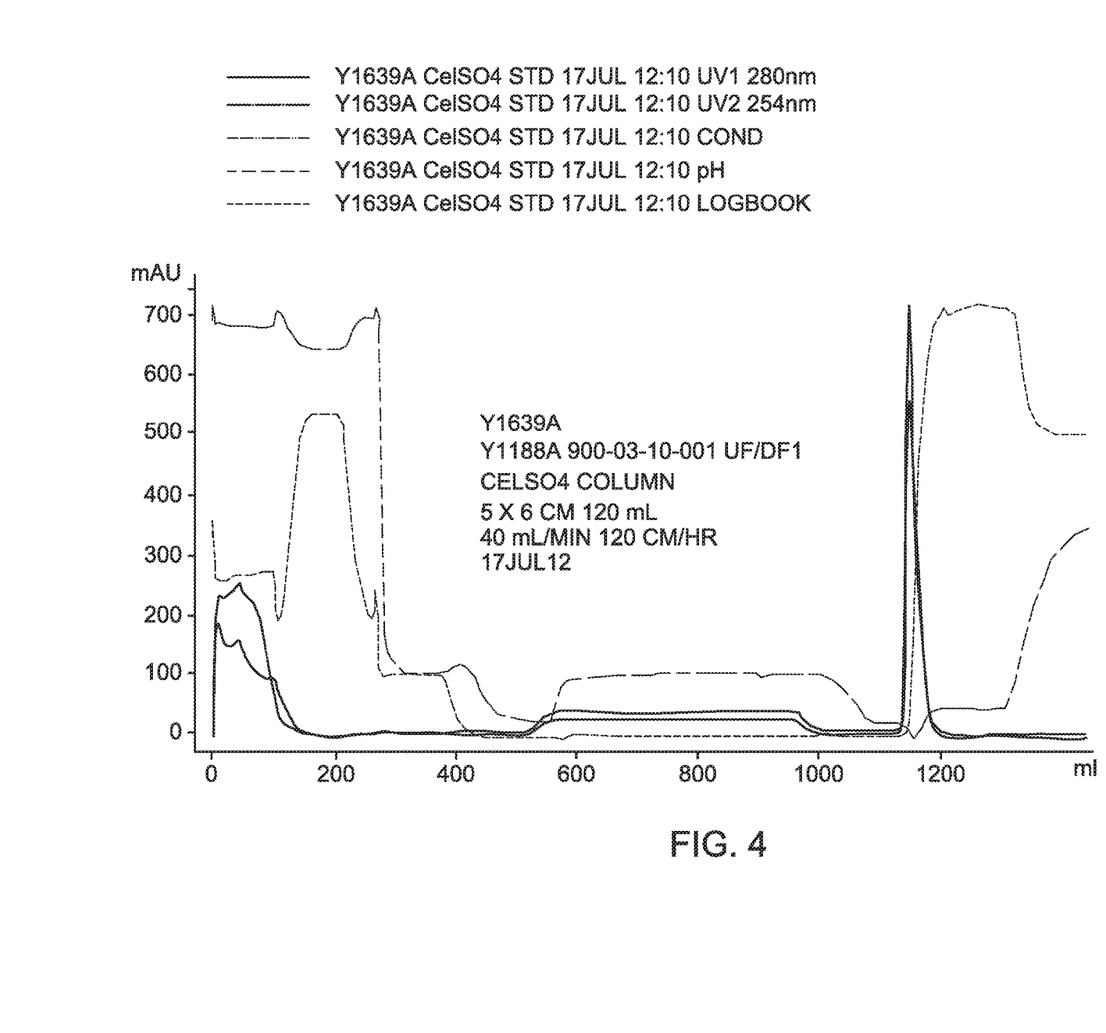
FIG. 4 is a process chromatogram for Experiment Y1639A using CELLUFINE® Sulfate column.
Figure 5:
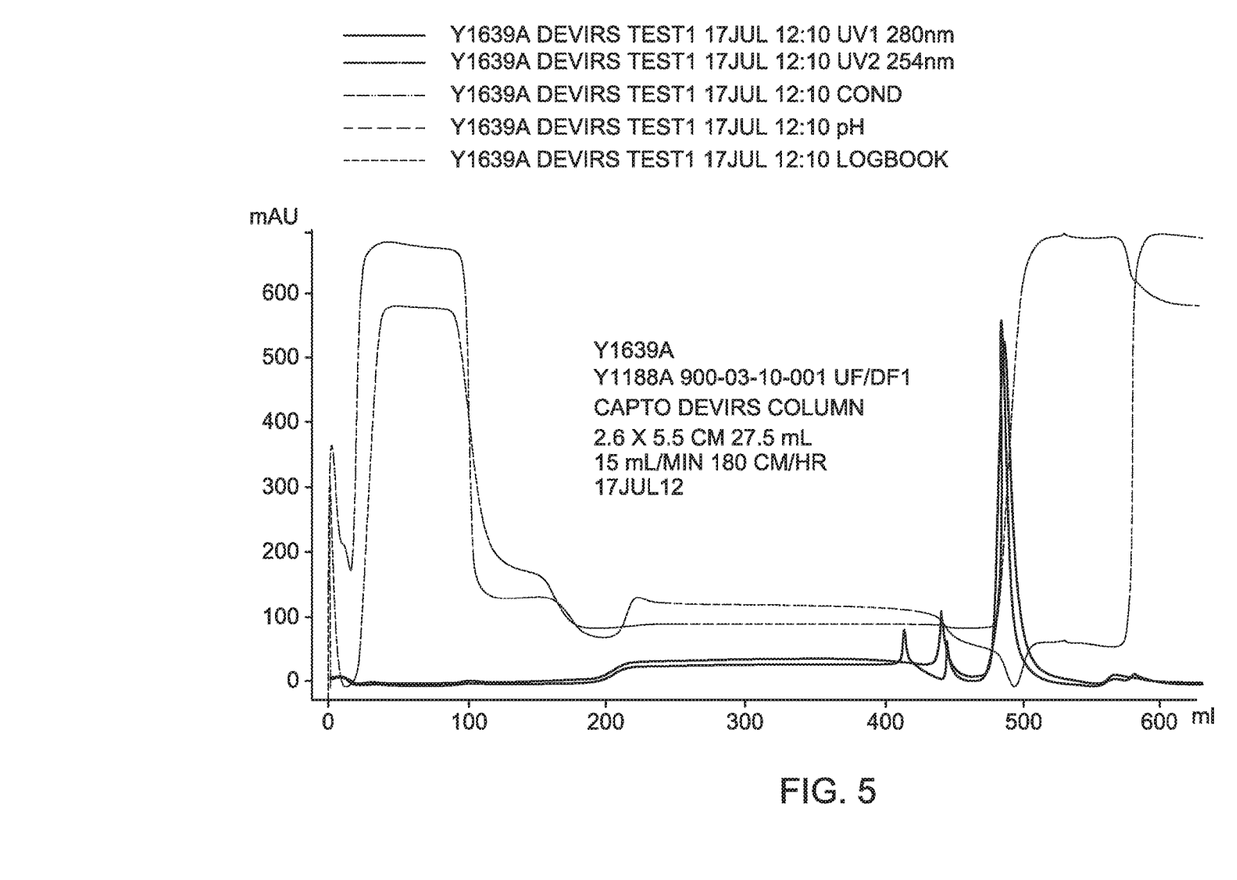
FIG. 5 is a process chromatogram for Experiment Y1639A using CAPTO™ DeVirS Column.

A process recovery chromatogram for Experiment 1639A using a CELLUFINE® Sulfate Column is shown in FIG. 4 and for Experiment 1639A using a CAPTO™ DeVirS column in FIG. 5.

Figure 8:
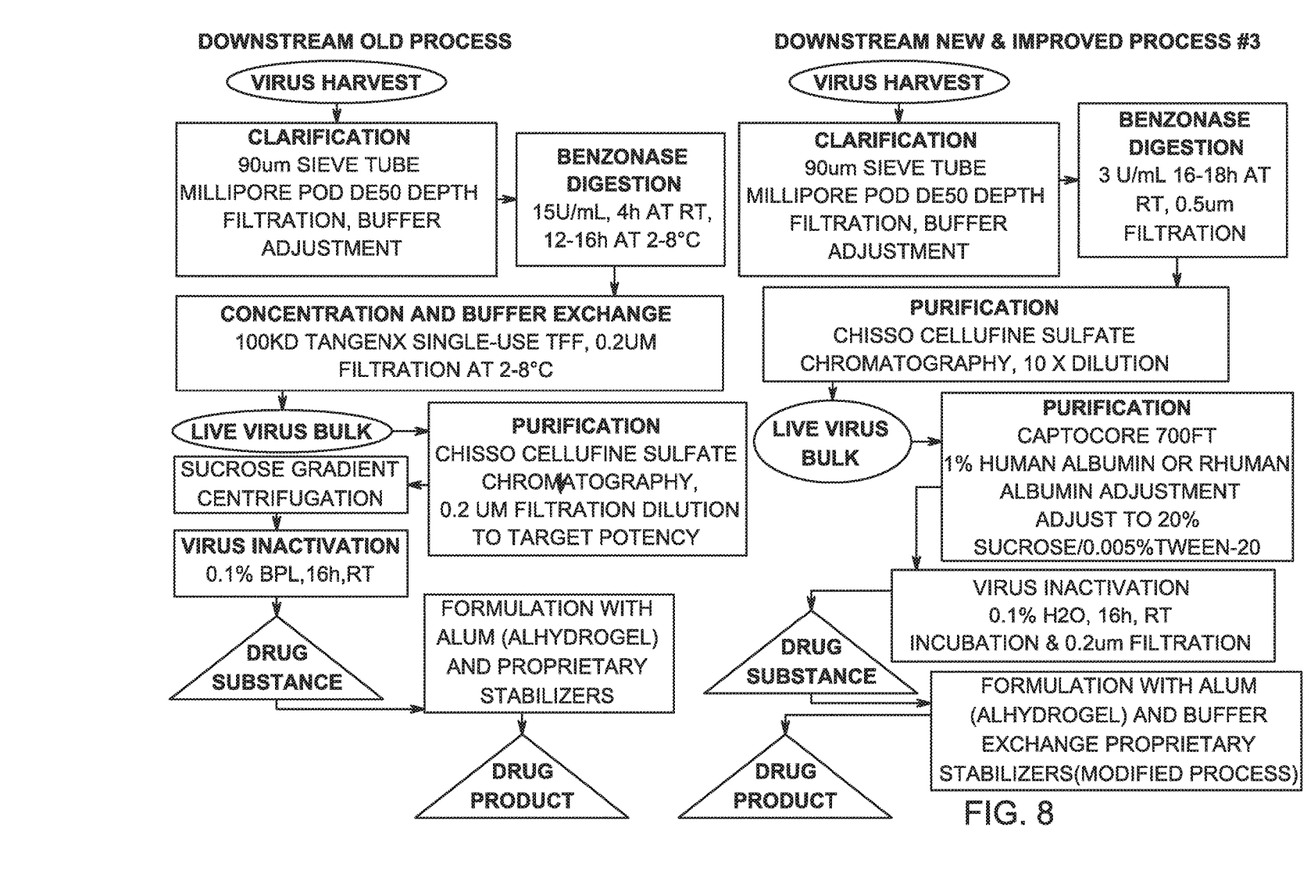
FIG. 8 is a flow diagram for another embodiment of an old downstream purification process and a flow diagram for an embodiment of the new and improved downstream purification process, Number 3.

Two other embodiments of the disclosed process are shown in FIG. 8, "Downstream new and Improved process #3."

It should be noted that the experiments were run using frozen/thawed materisl and that there was no non-GMP material remaining. We recommend using stored GMP material for further development of the disclosed process. However, the experimental results obtained with the non-GMP material demonstrate that the disclosed process significantly reduces HCP and DNA levels.

The disclosed chromatographic purification process yielded sufficient virus recovery and reduced the host cell protein levels to below the limit of detection of the commercial Vero cell HCP assay. These virus recoveries and HCP results were comparable to results achieved by a similar purification process utilizing sucrose gradient ultracentrifugation. A benefit of the disclosed process is that, unlike centrifugation methods, it is suitable for use in single-use systems.

The next phase of the Yellow Fever purification development is to replace the Chisso CELLUFINE® Sulfate resin with an equivalent GE Healthcare resin. The CELLUFINE® sulfate resin can potentially be replaced with GE Healthcare's CAPTO™ DeVirS resin. The CAPTO™ DeVirS is part of GE Healthcare's Custom Designed Media program, and is an affinity chromatography resin with the ligand dextran sulfate, which is known to have an affinity-like behavior to different types of virus. CAPTO™ DeVirS offers the a number of benefits for purification of virus, including, for example, excellent productivity, good chemical stability, and affinity-like behavior to various viruses.

The next planned experiments include following the use of CAPTO™ DeVirS with GE CAPTO™ Core 700. We will also investigate the use of an anion exchange membrane such as a Q Monolith (BIA) or a Q membrane (Natrix, Pall, Sartorius) between the step using the CAPTO™ DeVirS and the step using GE CAPTO™ Core 700.

EQUIVALENTS

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. A process for making an essentially pure inactivated flavivirus preparation comprising:
   a. obtaining a composition suitable for purification from a virus-infected Vero cell culture;
   b. clarifying the composition obtained in step "a" by removing cells and cell debris from said composition by depth filtration;
   c. subjecting the filtrate in step "b" to endo-nuclease digestion and 0.2 Micron Filtration sufficient to fragment Vero cell DNA followed by filtration;
   d. purifying the filtrate obtained in step "c" via a cross-linked agarose matrix with a dextran sulfate functional group chromatography resin and a cross-linked agarose matrix with an octylamine ligand chromatography resin having a shell that excludes molecules with a molecular mass greater than approximately 700 kDa from passing through pores of the shell to achieve depyrogenation of said virus in said filtrate;
   e. stabilizing and inactivating the viral product obtained in step "d" with an inactivating amount of β-PL;
   f. after inactivating the viral product in step "e", adjusting the temperature of the viral product to about 25° C. to about 30° C.;
   g. filtering the product obtained in step "f"; and
   h. formulating the product obtained in step "g" bound to alum.

2. The process of claim 1 wherein the flavivirus is Yellow Fever virus.

* * * * *